United States Patent [19]

Suzuki

[11] Patent Number: 4,495,634
[45] Date of Patent: Jan. 22, 1985

[54] X-RAY APPARATUS

[75] Inventor: Kenichi Suzuki, Kanagawa, Japan

[73] Assignee: Canon Kabushiki Kaisha, Tokyo, Japan

[21] Appl. No.: 370,848

[22] Filed: Apr. 22, 1982

[30] Foreign Application Priority Data

Apr. 28, 1981 [JP] Japan .................................. 56-64837

[51] Int. Cl.³ ...................... G01N 23/02; G03B 41/16
[52] U.S. Cl. .................................................. 378/173
[58] Field of Search ....................... 378/173, 174, 172

[56] References Cited

U.S. PATENT DOCUMENTS

3,891,850  6/1975  Bridgeman .......................... 378/173
3,991,317  11/1976  Kunne et al. ........................ 378/173
4,199,687  4/1980  Brendl et al. ....................... 378/173

Primary Examiner—Alfred E. Smith
Assistant Examiner—T. N. Grigsby
Attorney, Agent, or Firm—Toren, McGeady and Stanger

[57] ABSTRACT

In the disclosed device a film loader loads film sheets of different length to be exposed by X-rays. A transport arrangement transports the sheets to positions at which they are to be exposed. A holder keeps the upper edge of the film sheets at the same height in the exposure position regardless of the sheet length.

3 Claims, 17 Drawing Figures

X-RAY APPARATUS

BACKGROUND OF THE INVENTION

1. Field of the Invention

The present invention relates to an X-ray exposure device for medical purposes, particularly for exposing an X-ray image by selectively taking a sheet film from a magazine in which sheet films of different length are loaded and sending it to the exposure stage.

2. Description of the Prior Art

For economizing on energy, a popular type of X-ray film changer is designed so that a number of X-ray sheet films are loaded in a magazine, the sheet films are sent to an exposure stage one by one and retracted from the stage after an exposure is taken. However, in this changer the size of the film, the position of the film in the exposure stage and so have several restrictions.

However, the more popular the equipment becomes, the smaller in size users wish it to be.

Figure 1:
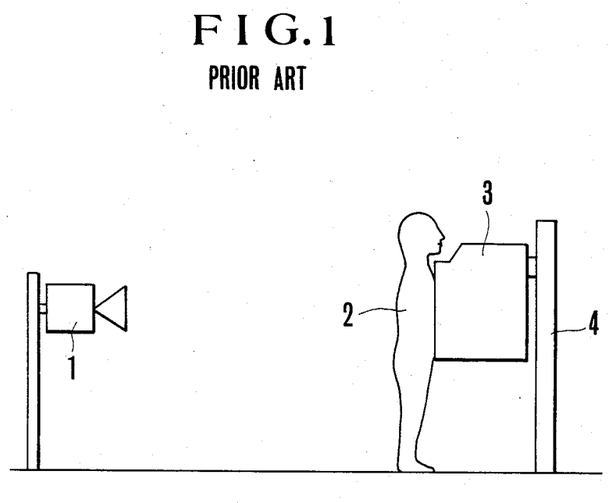
FIG. 1 shows an X-ray device for exposure of a chest.
Figure 2:
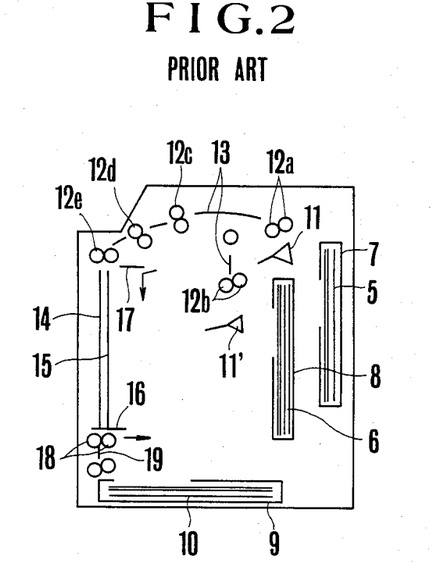
FIG. 2 shows the conventional device in section.

FIGS. 1 and 2 show an example of the conventional film exchanger for exposing a chest. This drawing includes an X-ray tube 1, a patient 2 to be inspected, a film changer 3 and a stand 4 for the film changer.

FIG. 2 shows the film changer 3 in section. In the drawing, film 5 is of the first size and film 6 the second size different in width from that of the first size film. A supply magazine 7 serves for the unexposed first size film, a supply magazine 8 for the unexposed second film, and a receive magazine 9 for receiving the exposed film 10. The side of each magazine is provided with a rectangular opening for receiving and delivering the films. Suckers or suction devices 11 and 11' are connected to the vacuum pump [not shown] and movable between the position in the drawing and the inside of the magazine with a transport mechanism. Rotatable rollers 12a–12e serve for transporting the film by holding it between them. A guide plate 13 guides the film along the transport route. A front fluorescent screen 14 fixed on the X-ray permeable fixing plate opposes a back screen 15. A sheet film is sandwiched between the screens and exposed. A film stopper 16 supports the lower edge of the sheet film. A film ejecting lever 17 ejects the sheet film after exposure, and a rotatable roller 18 and guide plate 19 transport the exposed film.

For exposing a chest in Japan films of the size 354 mm×354 mm and of the size 354 mm and 259mm are used, with the latter film the longer side being used vertically.

However, some patients cannot be exposed with film 354 mm×354 mm, especially if the chest and the abdomen are to be exposed at the same time, the chest and the clavicle are after wished to be inspected at the same time, and so on. Hence the opportunity for using the film 430mm×354 mm is becoming more and more frequent. Further in Europe as well as U.S.A. the 430 mm×354 mm film is usually used for exposing the chest. When film of the smaller size 303 mm×252 mm etc. is used for exposing children, a picture with too much wasted space to observe can be avoided. This also contributes to economy.

The conventional device shown in FIG. 2 is designed so that the sheet film which has been stopped with the stopper 16 is clamped between the screens. Hence the distance between the jaw pad of the changer and the upper edge of the film is too large when a film which is shorter than the standard one is used. Thus, it is necessary to raise the changer body in order to make the set position of the film correspond to the part of the patient to be inspected. However, when the changer body is raised the jaw of the patient hinders the exposing of the chest so that the chest of the patient is far from the changer body and it is difficult to obtain a sharp picture.

SUMMARY OF THE INVENTION

It is an object of the present invention to transport the sheet film surely and set it at a determined position in the exposure stage.

It is another object of the present invention to keep the upper edge of the film at the same position in the apparatus to be set vertically even when a sheet film is exchanged for another one with different length.

It is a third object of the present invention to realize an effective cooperation of the film transportation mechanism with the sheet film holding mechanism.

DESCRIPTION OF THE PREFERRED EMBODIMENTS

Figure 3:
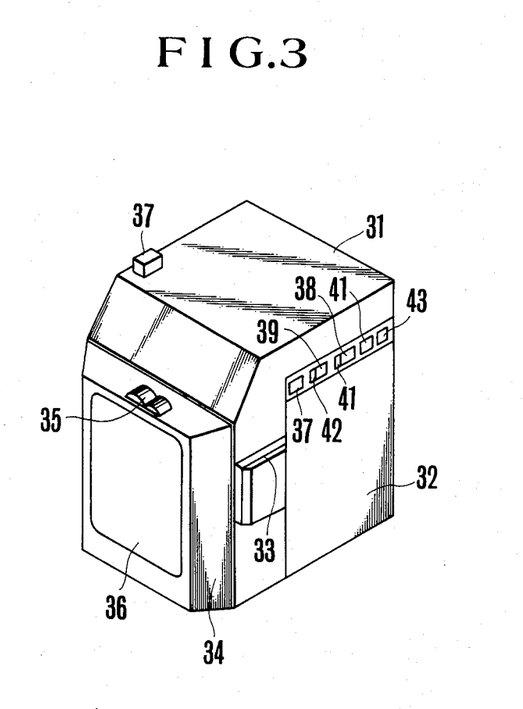
FIG. 3 shows an embodiment in perspective view.
Figure 4:
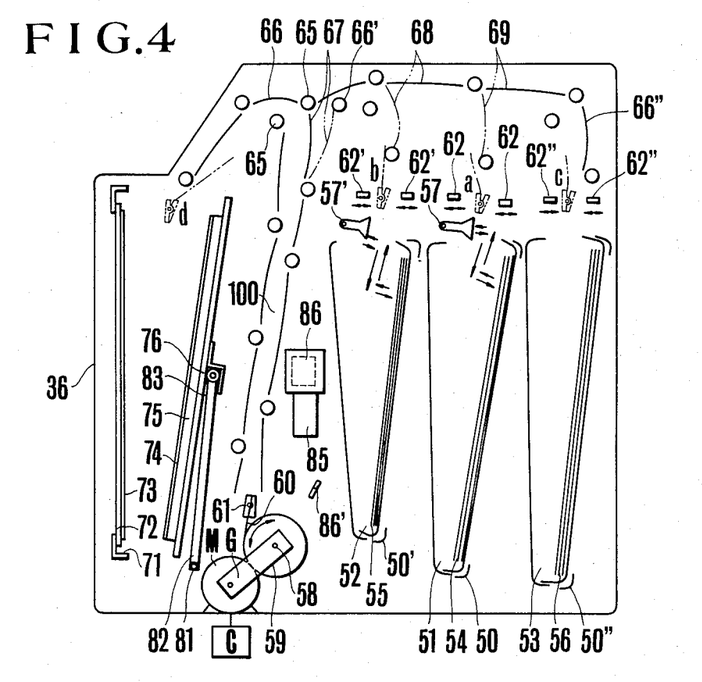
FIG. 4 shows a section of FIG. 3.

FIG. 3 shows the external appearance of a first embodiment of the invention, while FIG. 4 is a section of this embodiment. These figures include a chest film changer body or housing 31 and a door 32 for a magazine loading portion arranged on the housing 31 so as to be opened when the magazine is put in or taken out.

A slit 33 is arranged to receive an ID card bearing the information of a patient and this information is to be superimposed on a film. A chin pad 35 is arranged to support the chin of the patient. A chest plate 36 is made of material through which an x-ray passes easily.

A lamp 37 lights up when it is ready to take a photograph and lamps 38, 39 and 40 light up when a magazine is inserted. The lamp 38 corresponds to the supply magazine for the first size films, lamp 39 to that for the second size films and lamp 40 to the receive magazine. A switch 41 starts feed of the first size film , a switch 42 serves for starting to feed the second size film and a switch 43 for closing the cover of the inserted magazine (not shown in the drawing).

In FIG. 4, a supply magazine 51 has the first size of unexposed films loaded therein, a magazine 52 is that in which the second size unexposed films are loaded and a receive magazine 53 receives the exposed films. The magazines open at the one side of the cover and the casing, and are held with holding rails 50-50". The first size unexposed films 54 and the second size unexposed films 55 have lengths and in some cases widths which are different.

Members 56 are the exposed films. Sucking disks or suction devices 57 and 57', which suck the films one by one, are moved as is shown by the arrow in the drawing with the mechanism not shown. That is, after having entered into the route, they sink into the magazine, advance toward the film, suck the film and return along the reverse direction. A rotatable shaft 51 is arranged to be driven by a pulse motor M via a gear train G. The pulse motor is reversible and controlled by the motor control circuit C so that after a certain number of rotations (corresponding to a number of pulses) it stops.

A second drum 58 rotates on the shaft 59 rotates on the shaft 58 and a flexible feed sheet 60 composed for example of a thick sheet of synthetic resin is wound on the drum 59 and has clips 61 for holding the film at the end.

For example two clips 61 are provided at the same distance from the side of the sheet 60, each having a needle shaped projection for preventing the films from falling down. The clips urge nippers with springs but it is also possible to urge them with magnets.

Members 62, 62' and 62" serve for opening and closing the nippers of the clips 61 and are arranged near the respective magazines and moved with the mechanism [not shown]along the directions of the arrows.

A rotatable roller is located opposite guide plates 66, 66' and 66" which serve for guiding the film and the transportation sheet. Inducing plates 67, 68 and 69 have one end rotatably supported and another end which is moved with the mechanism not shown so as to induce the films and the transportation sheet 60 along predetermined routes.

A securing member 71 is empty in the exposure range and has an X-ray permeable support member 72 for a front screen 73 provided thereon. The front screen 73 is supported by the screen support member 72. A sponge 75 serves for bringing a back screen 74 into contact with the film, and to press them evenly. A press plate 76 holds the back screen 74 and the sponge 75 in sequence.

A shaft 81 is fixed and a lever 82 is arranged on the fixed shaft 81 so as to be rotatable and swung along the direction of the arrow with means [not shown ] to push the press plate 76 against the screen support member 72 or pull it. A bearing 83 is provided in the lever 82. A lens barrel 83 and mirrors 86 and 86' serve to superimpose the information on the ID card inserted in the slit 33 upon the film.

A pull-in route has a length capable of loading the longest sheet film.

In operation, sheet films are loaded in the supply magazine 51 and 52 and put in the film changer body 31 after opening the door 32. At this time the clips 61 and suction devices 57 and 57' assume the positions of the solid lines, the inducing plate 67 the position of the two dot dash line and the inducing plates 68 and 69 the positions of the solid line. When the feed switch 41 is depressed the inducing plate 69 moves to the position of the two dot dash line, while the magazines 51, 52 and 53 open with the [not shown]engaging means.

After that, the drum 59 is rotated clockwise and the transport sheet 60 is rewound once and pulled out, while the clips 61 move to the position of the two dot dash line a along the route formed by the inducing plates 68 and 69. Then the suction device 57 at the side of the supply magazine 52 of the first size is successively moved along the direction of the arrows in the drawing.

At this time the opening member 62 pushes the clips 61, whose end opens. The suction device 57 which is actuated with the not shown vacuum pump sucks one sheet film and returns to the position in the solid line so as to insert the film sheet in the opened ends of the clips. Then the opening member 62 leaves the clips 61, whose ends hold the film sheet.

When the suction device 57 stops sucking, the film leaves the suction device and at the same time the suction device moves along the direction along which the suction device leaves the film. Further, in case the feed switch 42 is depressed instead of the switch 41, the inducing plate 68 moves to the position in the two dot dash line, while by means of the not shown means the magazines 51, 52 and 53 open. Then the drum 59 rotates clockwise and the clips move to the position in the two dot dash line b. The suction device 57' at the side of the supply magazine of the second size successively moves along the direction of the arrows in the drawing and carries out the same movement as when the feed switch 41 is pushed. In this way the clips 61 hold one film sheet. Then the drum 59 rotates counterclockwise so as to wind the feed sheet, while the clips which hold the sheet film move to the position in the solid line in the drawing so as to pull the sheet film into the pull-in route 100. Then the inducing plate 67 moves to the position in the solid line. Then, when the drum 59 rotates clockwise the clips 61 push the film into the position in the two dot dash line d, always keeping a predetermined distance.

Thus, the sheet film enters between the screens 73 and 74, while the upper edge of the film sheet is kept at the determined height. Then the lever 82 rotates counterclockwise and the screens 73 and 74 closely sandwich the sheet film.

The X-rays are radiated to and from the object. When an exposure has been taken the lever 82 rotates clockwise so as to open the screens 73 and 74. Then the drum 59 rotates counterclockwise and the clips 61 which hold the sheet film move to the position in solid lines in the drawing so as to pull the film into the pull-in route.

Then the lamp [not shown]lights and the information on the ID card is superimposed on the film.

Then, the inducing plate 67 moves to the position in the two dot dash line, while the inducing plates 68 and 69 move to the solid line in the drawing. The drum 59 rotates along the clockwise direction and the clips which hold the sheet film move to the position in the two dot dash line c. Then the opening members 62" push the nippers of the clips, whose ends open, when the film sheet falls down in the receive magazine 53.

Then, the opening members 62" leave the clips, the drum 59 rotates counterclockwise, the clips move to the position in solid lines and one exposure is completed. If it is desired to take another exposure, the above operation is repeated when the switch 41 or 42 is depressed again. The magazine remains opened. When the exposure is completed or the film is to be developed, the covers of the magazines are closed and the door 32 opens with the mechanism [not shown] when the switch 43 is depressed.

When the drum 59 is rotated with the pulse motor in the present invention the pulse motor is operated with a certain determined number of pulses so as to determine the amount of advance of the clips. However, it is possible to provide a detector at the position at which the clips have to stop in order to stop the motor by detecting that the clips reach the position or to provide a chopper on the shaft of the drum of a shaft operatively engaged with the shaft and a detector for counting of the chopping number of the chopper in order to stop the motor when the chopping number reaches a certain value.

In one practical embodiment the system is arranged horizontally for the convenience of a patient in bed.

Figure 5:
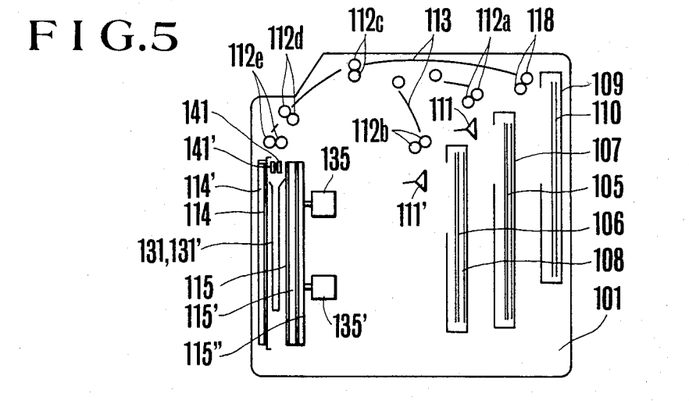
FIG. 5 shows a second embodiment in section.
Figure 6:
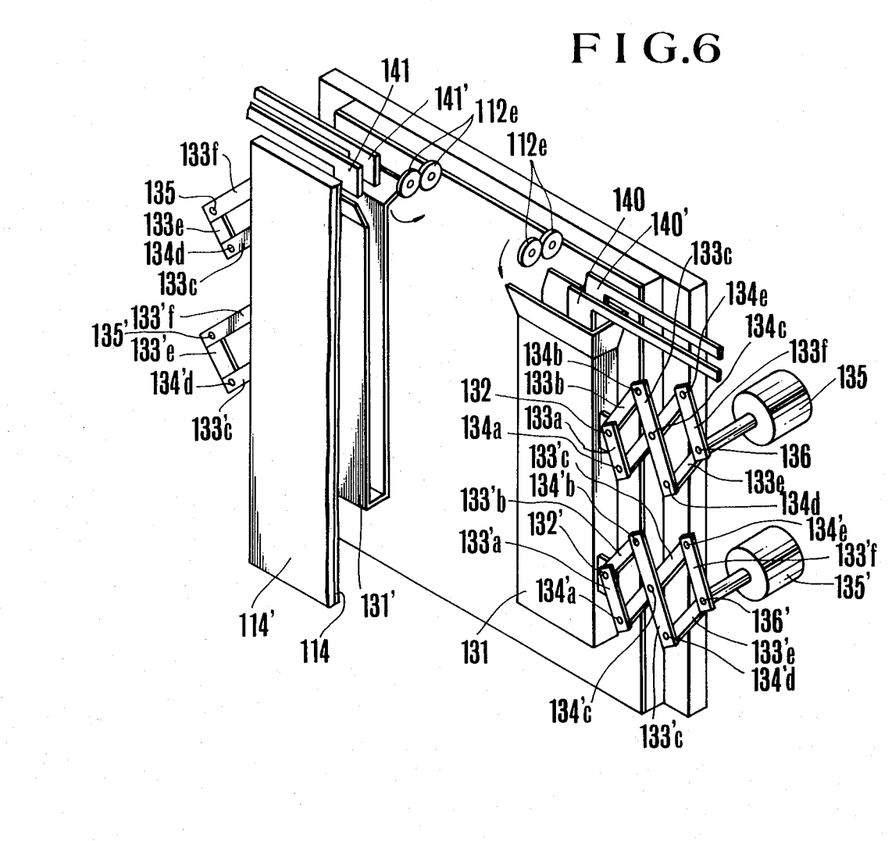
FIG. 6 shows important parts of FIG. 5 in perspective view.

FIGS. 5 and 6 show a second embodiment. This includes a changer body 101, the first size film 105 and the second size film 106 different in length from that of the first size film. Member 107 is a supply magazine for loading the unexposed first size film, 108 a supply magazine for loading the unexposed second size film, 109 a receive magazine for receiving the exposed films and 110 the exposed films. At the side of each magazine a rectangular opening serves for loading and unloading the films. Suckers 111 and 111' connected to a suction pump [not shown] are movable between the position in the drawing and the inside of the magazine with a suitable moving means. Rotatable rollers 112a–112e serve for moving the film sandwiched between them. A guide plate serves for guiding the film along the transport route. Front screens 114 are secured on the X-ray permeable fixing plate 114'. Back screen 115 is secured on the X-ray permeable movable fixing plate 115" via a cushion 115'.

Film support boxes 131 and 131' are open upward and sideward, while the open sides of the boxes are opposed to each other. The film support boxes 131 and 131' are movable along the horizontal direction between the screens 114 and 115 in such a manner that when they approach each other a thin box open upwards is formed so that the even curled film can enter it when the film is fed as is explained later.

Rotation shafts 132 and 132' are provided on the projections of the film support box 131, and levers 133a–133f and 133'a–133'f are rotatably mounted with the shafts 134a–134f and 134'a and 134'f so as to form pantographs connected to the rotation shafts 132 or 132'. Members 135 and 135' are positional servo-motors whose rotation amount is determined with a position control circuit. Pins 136 and 136' on the rotation axes of the servo-motors 135 and 135' are connected to the other ends of the pantographs. The pins are firmly connected to the levers 133f and 133e or 133'f and 133'e and loosely to the others, and the levers 133f and 133'e are fixed to the housing (not shown).

Although shown only partially in the drawing a similar pantograph and similar servo-motors are connected to the film support box 131'. By properly rotating the positional servo-motor the film support boxes 131 and 131' can be symmetrically advanced and retracted in such a manner that the sheet film can be properly held between the screens 114 and 115 or the screens and the sheet film can be brought in close contact. Further, although the lift mechanism is not shown, it is convenient to handle sheet films of different length if the servomotors 135, 135' are arranged to be lifted in accordance with the length of the sheet films.

Sets of levers 140 and 140' and 141 and 141' serve for temporarily holding the upper end of the film, and are closed or opened with a mechanism [not shown] and are further movable forwards, backwards, upwards and backwards while holding the sheet film.

The operation of the above construction is as follows. The sucker 111 and 111' suck the unexposed films 105 or 106 one by one and insert them in the roller 112a or 112b. The rollers 112a or 112b and 112c and 112d rotate so as to transport the film between the screens 114 and 115. At this time the holding levers 140, 140' and 141, 141' are open. Further, the film support boxes 131 and 131' receive the film fed with the rollers. The upper end of the sheet film is adjusted in advance with the servo-motors 135 and 135' so as to correspond to the upper end of the screens. When the sheet film leaves the roller 112e and falls down in the film support box, the holding levers 140, 140' and 141, 141' firmly clamp the upper end of the sheet film and then the servo-motors 135 and 135' rotate so as to bring the film support boxes 131 and 131' out of the exposure field. After that the back screens support plate 115" moves forwards and the sheet film is closely sandwiched between the screens 14 and 15. At this time the holding levers 140, 140' and 141, 141' which hold the sheet film move forwards together with the back screen 115.

So far the exposure is ready. After finishing the exposure the back screen resumes the initial position, while the levers 140, 140' and 141, 141' also move backwards. Then the levers which hold the exposed film move upwards and insert the edge of the film between the wheels of the roller 112e. At this time the rollers 112e stand still. The rollers 112e rotate along the direction of the arrow in FIG. 6 with a one way clutch but can not rotate in the reversed direction so that the film never falls down even if the hold levers open after the film has been clamped with the rollers 112e. Then the rollers 112e rotate along the direction of the arrow, while the rollers 112d and 112c rotate along the reversed direction, and the roller 118 rotates so as to lead the sheet film into the receive magazine 109.

In the present embodiment, a box shaped arrangement which is vertically long is used as the film support member, so there is no fear that the sheet film which falls down between the screens should not pass downwards between the film support plate and the screen even if the sheet film is curled. Further, the film support plate is a mere even plate it is advisable to fix a soft member such as sponge on the edge of the support plate in order to fill up the space between the film support plate and the screens, so it is possible to move the support plate without damaging the surface of the screens. Further, even when the sizes of the sheet film are more than three, the vertical position of the support plate is made to change over more than three steps so that the upper edge of the screens can be made to correspond to that of the sheet film while a conventional stopper can be made use of for the longest sheet film. On the other hand the sheet film can be loaded in the receive magazine in a conventional way, while the sheet film can be transported with belts instead of rollers.

Figure 7:
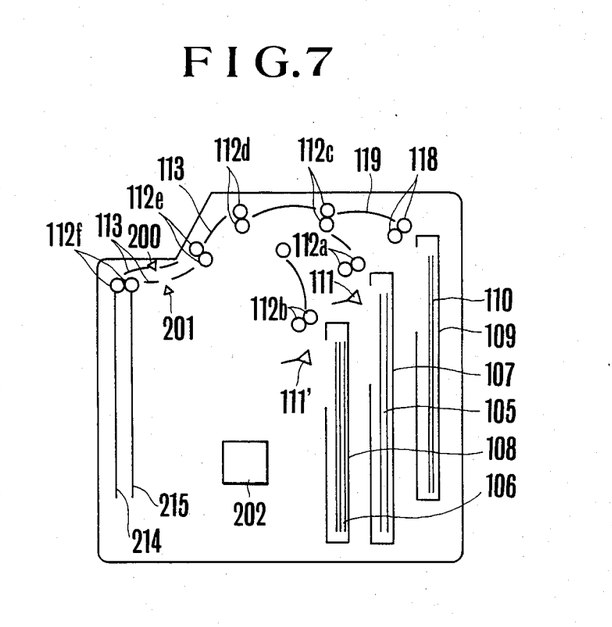
FIG. 7 shows a third embodiment in section.
Figure 8:
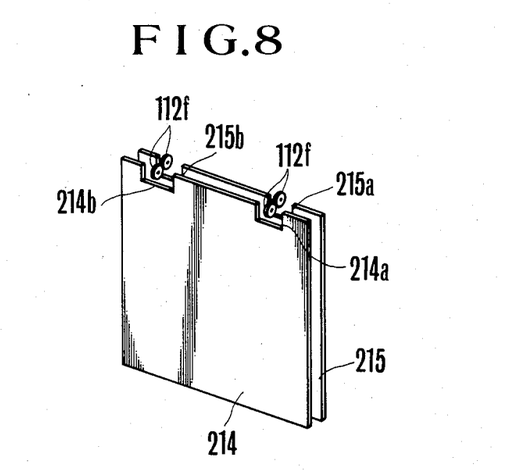
FIG. 8 shows important parts of FIG. 7 in perspective view.

FIGS. 7 and 8 show the third embodiment. The members having the same reference figures as those for the aforementioned embodiments are the same members. Members 113 and 119 are the guide plates of the sheet films and 112f rollers. A photosensor 201 serves for sensing the light which comes from the light emitting element 200 does not expose the sheet film in order to detect the time point at which the sheet film passes by sensing the light. A pulse motor 202 drives the rollers 112a–112f via a driving mechanism [not shown]. Support plates 214 and 215 each provided with a screen, have notches 214a, 214b, 215a, 215b for receiving the roller 112f, as is shown in perspective view in FIG. 8. Further, the support plate 215 is movable forwards and backwards in the same way as in the afore-mentioned embodiment.

When the unexposed film 105 or 106 is fed through the rollers 112a–112e in the above construction, the photosensor detects the rear edge of the sheet film when the sheet film passes between the guide plates 113, at which moment the detection signal is sent to the pulse motor 202 so as to drive the motor with a number of pulses that produce rotations. This pulse number is determined to correspond to the time from which the rear edge of the film passes the position of the photosensor till it reaches the upper edge of the screen.

Because the last roller 112f stops, holding the upper edge of the sheet film when the pulse motor stops, the upper edge of the sheet film corresponds to that of the screen. Then the roller 112f holding the film and the back screen 215 advance at the same time, while the front screen is brought in close contact with the sheet film.

When the film has been exposed to the X-rays in this state the back screen 215 and the roller 112 resume the original positions, and the rollers 112f–112c rotate along the reverse direction, while the roller 118 rotates along the same direction so as to deliver the exposed sheet film into the receive magazine 109.

Figure 9:
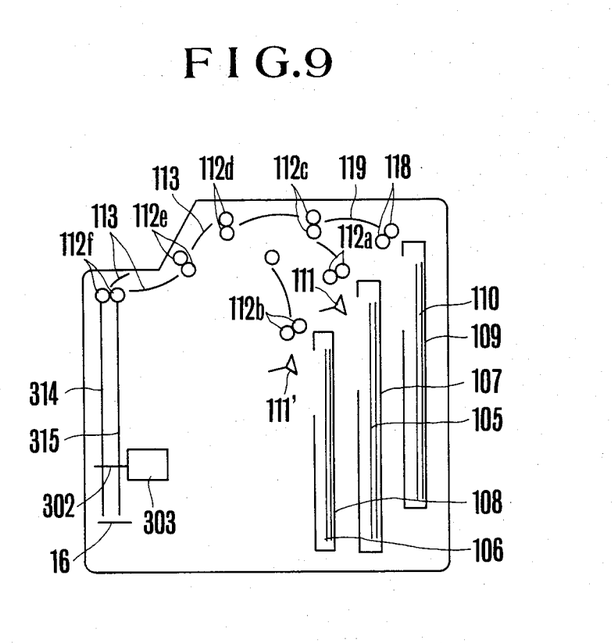
FIG. 9 shows a fourth embodiment in section.
Figure 10:
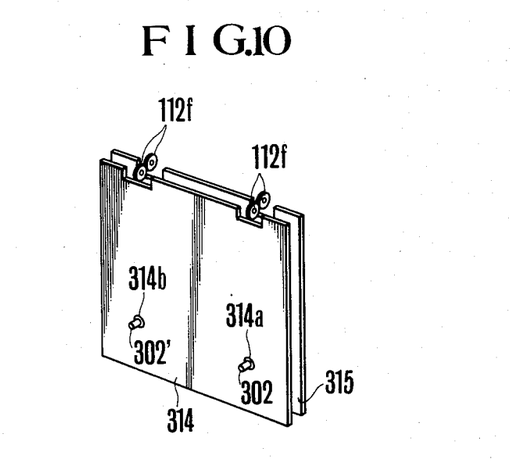
FIG. 10 shows important parts of FIG. 9 in perspective view.

FIGS. 9 and 10 show a fourth embodiment. The members having the same figures as those for the aforementioned embodiments are also the same members. Needles 302 and 302' penetrate the front and the back screens even when they are most distant. The needles are inserted into and retracted from the screens with the advance and retraction mechanism 303. The screen and its support plate have small holes 114a and 114b through which the needles pass.

Further, the advance and retraction mechanism is arranged so that when the short sheet film is selected with the sheet film size selector, the needles are advanced so as to support the short sheet film, and the upper edge of the sheet film corresponds to that of the screen. Further, in case of the normal long size sheet film the conventional stopper 16 is used, and the advance and retire mechanism 303 loads the needles.

In the above construction the sheet film is fed with the rollers 112e and also the rollers 112f. The roller 112f which holds the film rotates for a predetermined time and stops when the sheet film is stopped with the needles 302, 302' or the stopper 16. Then the back screen 315 advances and closely sandwiches the film between itself and the front screen 314 so that the roller 112f which holds the film advances together with the back screen.

When the exposure is taken the back screen 315 and the roller 112f retire into the original position the roller 112f which has firmly held the sheet film rotates in the reverse direction so as to deliver the exposed sheet film into the receive magazine 109 in cooperation with the other rollers.

In order to load the exposed sheet film in the receive magazine, it is possible to arrange the receive magazine under the stopper 16 in such a manner that the sheet film could fall down into the receive magazine through the upper edge of the magazine with the force of gravity.

Figure 11:
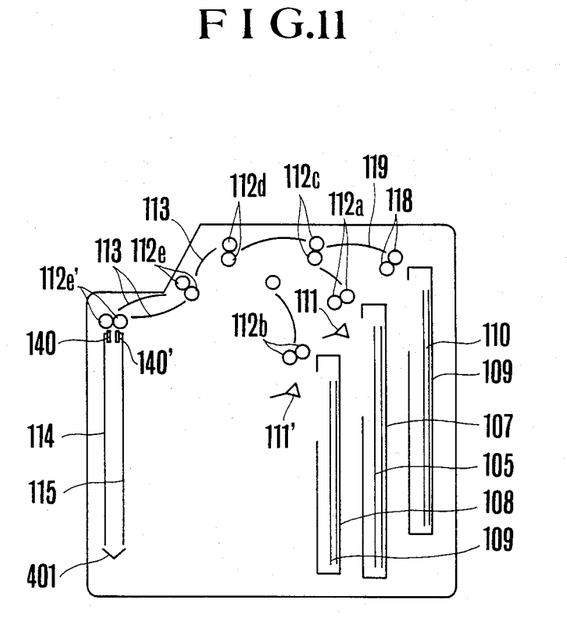
FIG. 11 shows a fifth embodiment in section.
Figures 12, 13:
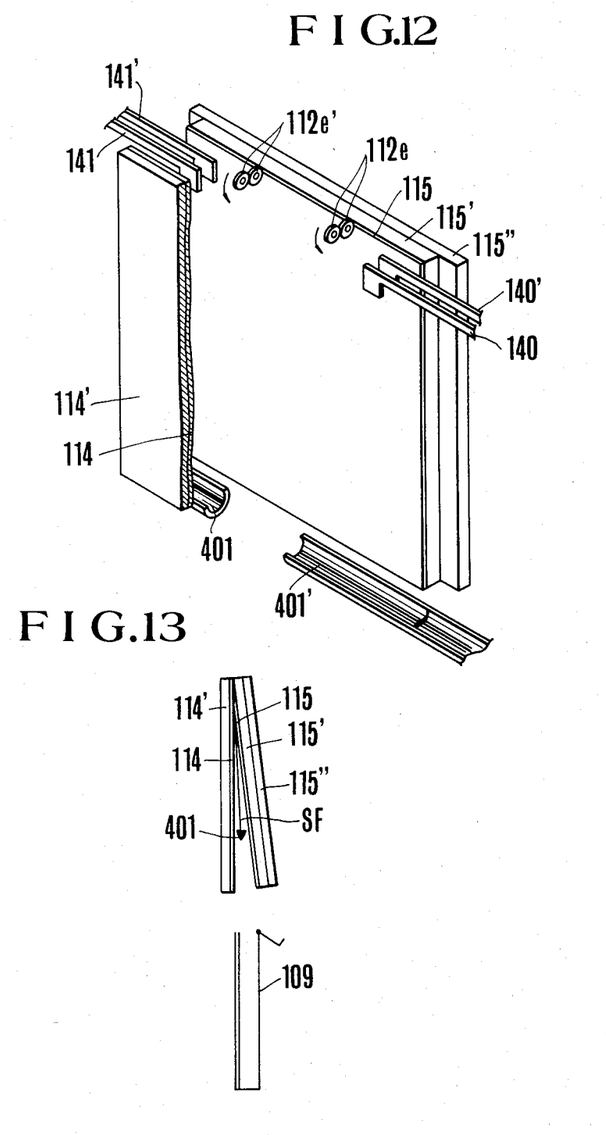
FIG. 12 shows important parts of FIG. 11 in perspective view.
FIG. 13 shows a sixth embodiment in partial section.

FIGS. 11 and 12 show a fifth embodiment. The members here having the same reference numerals as those for the aforementioned embodiments are the same members. In FIGS. 11 and 12, the support bars 401 and 401', each having a V groove at the end are movable forwards and backwards and upwards and backwards. Further, levers 140, 140' and 141, 141' are the same as holding levers shown in FIG. 6. Rollers 112e' and 112e are the feed rollers.

The sheet film which is brought out of the supply magazine 107 or 108 is stopped in the middle with the support bars 401, 401', which are raised up to the position at which the upper edge of the sheet film corresponds to that of the screens. Then the holding levers 140, 140' and 141, 141' hold the upper edges of the sheet film, when the support bars 401, 401' retire out of the exposure range and go down in order to prepare for the next exposure. When the support bars have retracted the back screen 115 advances together with the holding levers so as to sandwich the sheet film between the back screen and the front screen.

When the exposure has been taken the back screen 115 and the holding lever resume the original position, the holding levers go up a little so as to sandwich the sheet film between the rollers 112e for further transportation.

FIG. 13 shows an important part of a variation of the above embodiment. In this sixth embodiment the holding levers are omitted. Instead of the holding levers, the upper edge of the front screen 114 comes in contact with that of the back screen 115 and then their entire surfaces come in contact with each other. Specifically, when the support bars 401, 401' support the sheet film SF, the upper edge of the back screen 115 comes in contact with the front screen 114 so as to hold the sheet film temporarily. When then the support bars retract the lower edge of the back screen 115 comes in contact with the front screen in such a manner that the screens come in contact with the sheet film over their entire surfaces. In this embodiment, the exposed sheet film falls down into the receive magazine 109.

Figure 14:
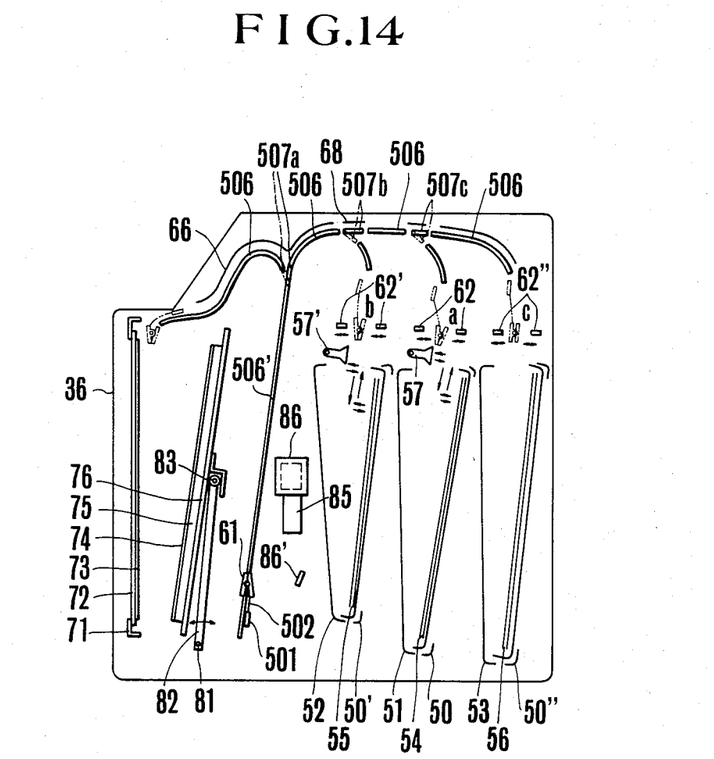
FIG. 14 shows a seventh embodiment in section.
Figure 15:
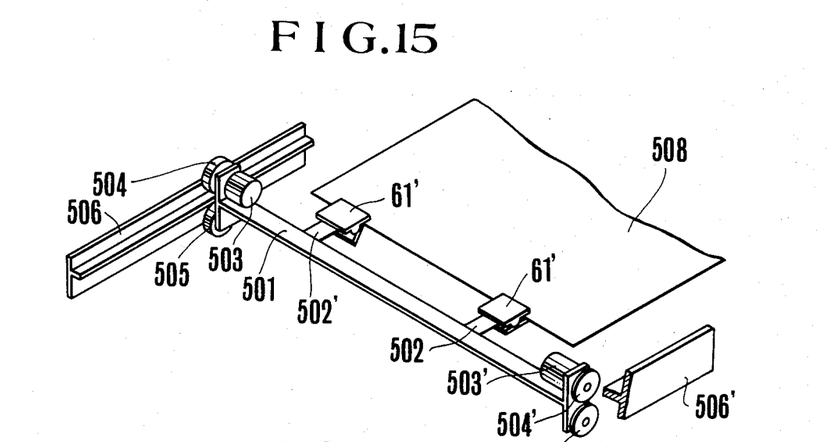
FIG. 15 shows important parts of FIG. 14 in perspective view.

FIGS. 14 and 15 show a seventh embodiment. The members having the same reference numerals as those of the embodiment in FIG. 4 are the same members and have the same functions. In FIG. 15 a transport bar 501, is longer than the width of the widest film. The transport bar 501 carries two strong flexible strips 502 and 502' each having a clip 61, 61' at its end. Further, from the both ends of the transport bar 501, flanges extend up and downwards, to bear the wheel 504, 505 and 504', 505'. Of these, wheels 504 and 504' are respectively mounted on the rotation axis of the small motors 503, 503' provided on the back sides of the flanges. Further, the wheel sets 504, 505 and 504' and 505' lightly clamp the guide rails 506, 506'. Thus, when the small motors 503 and 503' operate, the transport bar 501 moves along the guide rail.

The guide rail 506 is secured on the wall of the housing as is shown in FIG. 14, while on the way of the guide rail the change over rails 507a, 507b, 507c for changing over the routes are arranged so as to induce the transport bar 501 at the desired position. The position in a solid line or that in a dotted line can be selected with the remote control.

In the above-mentioned construction, the clips 61, 61' are first stopped at the position a or b and the sheet film is held in the clips 61, 61' with the same operation as explained in connection with the first embodiment. Then the transport bar 501 retires into the pull-in guide rail 506 and then moves to the position d from the side of the sheet film so as to insert the sheet film between the screens 73 and 74. In this case the upper edge of the sheet film is kept at the same position irrespective of the length of the sheet film. When the exposure has been taken, the transport bar 501 again retracts in the pull-in guide rail, advances toward the receive magazine 53 from the side of the sheet film, stops at the position c, and opens the clips 61, 61' to allow the exposed sheet film to fall down into the receive magazine.

Figure 16:
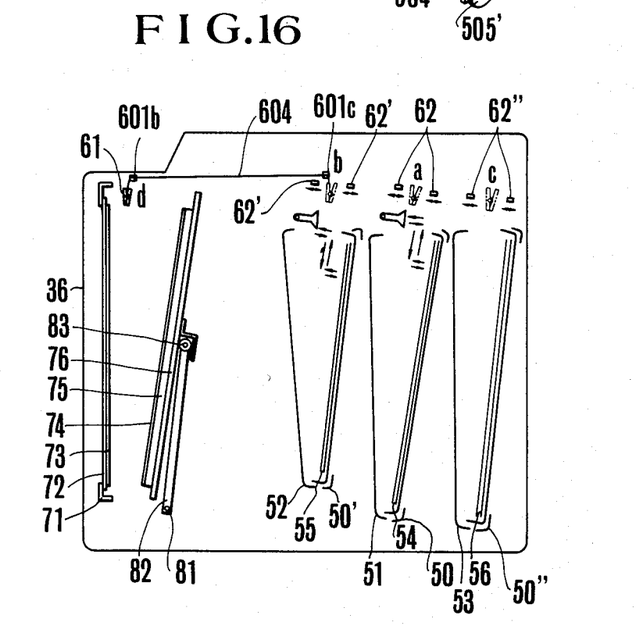
FIG. 16 shows an eighth embodiment in section.
Figure 17:
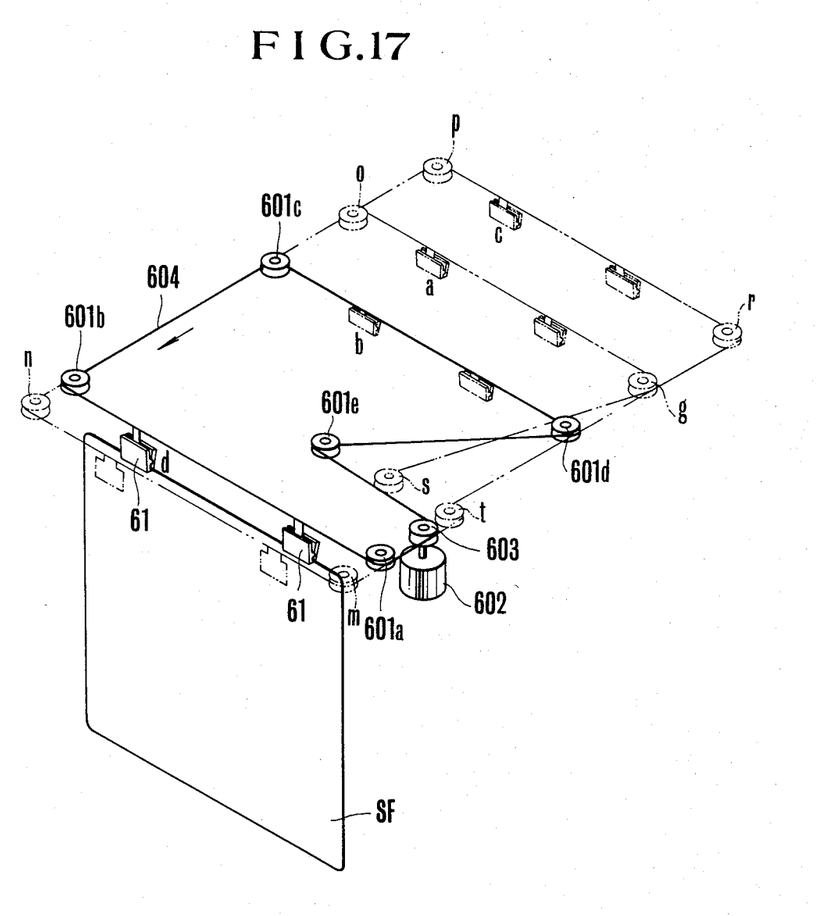
FIG. 17 shows important parts of FIG. 16 in perspective view.

FIGS. 16 and 17 show an eighth embodiment, FIG. 16 in section, and FIG. 17 the important part in perspective view. In the drawing pulleys 601a, 601b are rotatable and respectively movable between the position in the drawing and m and n by means of the [not shown] moving mechanism. Further, of rotatable pulleys 601c–601e pulley 601c is movable from o to p, 601d from q to r and 601e to s or t.

A driving pulley 603 is driven by a motor 602. A wire 604 over the pulleys 601a–601e and 603 is fixed to the clips 61, 61'.

In the above-mentioned construction, the clips 61, 61' are set at the position a or b. This operation is realized by making the pulleys 601c and 601d select the position o and q and the step for driving the motor 602 to move the wire and making the clips stop at the desired position. Then, as has been described, after the exposed sheet film has been clamped with the clips 61, 61', the motor 602 is driven to pull the wire along the direction of the arrow so as to move the clips 61, 61' up to the position d.

The sheet film is closely sandwiched between the screens 73 and 74, and along with the advance of the back screen 74 the pulley 601a moves to the position m, while the pulley 601b advances up to the position m. At this time the pulley 601e moves to the position s in order to compensate the change of the length of the wire.

When the exposure has been taken, the pulleys 601a and 601b resume the original position, the pulley 601c moves to the position p, the pulley 601d to the position t. When the pulleys have moved to their respective positions, the motor 602 rotates so as to make the pulley deliver the wire along the counter direction of the arrow, whereby the clips 61, 61' which hold the exposed sheet film move to the position c and open so that the sheet film is received in the receive magazine 53.

In the case of the present embodiment a combination of the pulleys with the wire is used. However, the combination of the gears with the chain will also do.

What is claimed is:

1. An X-ray apparatus comprising:
   converting means for exposing a sheet film disposed perpendicular to the horizontal direction;
   film loading means for loading sheet films of different length;
   transporting means for transporting a sheet film from the film loading means to the converting means along a descending direction; and
   holding means for keeping the upper edge of the sheet film substantially at the same height in the converting means regardless of the length of the sheet film.

2. An X-ray apparatus in accordance with claim 1, wherein the transporting means is provided with flexible means, guide means for guiding the flexible means and operation means for advancing and retiring the flexible means.

3. An X-ray apparatus in accordance with claim 2, wherein the flexible means is a plastic belt.

* * * * *